United States Patent [19]

Akerkar et al.

[11] 4,202,874
[45] May 13, 1980

[54] MONORADIOIODINATED DERIVATIVES AND PRECURSORS FOR PRODUCTION THEREON

[75] Inventors: Anandrao S. Akerkar, Pomona, N.Y.; Herman Rutner, Hackensack, N.J.

[73] Assignee: Becton Dickinson & Company, Paramus, N.J.

[21] Appl. No.: 885,447

[22] Filed: Mar. 10, 1978

Related U.S. Application Data

[62] Division of Ser. No. 727,407, Sep. 29, 1976, Pat. No. 4,120,867.

[51] Int. Cl.$^2$ .................... G01N 33/16; A61K 43/00
[52] U.S. Cl. ...................... 424/1; 23/230 B; 252/408; 260/112 B; 424/12
[58] Field of Search ............ 260/326.4, 570.8 R, 260/309, 112 R, 112 B; 560/29, 39, 75; 562/438, 437, 445, 446, 444, 465; 23/230 B; 424/1, 12; 252/408

[56] References Cited

U.S. PATENT DOCUMENTS

| | | | |
|---|---|---|---|
| 3,925,355 | 12/1975 | Piasio et al. | 424/1 |
| 3,957,963 | 5/1976 | Salmon et al. | 424/1 |
| 3,989,812 | 11/1976 | Barrett et al. | 260/112.5 R |
| 4,120,867 | 10/1978 | Akerkar et al. | 260/326.4 |

OTHER PUBLICATIONS

Bolton et al., Biochem. J. (1973) 133, 529–539.

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

Monoradioiodinated derivatives of compounds employed in a radioassay prepared from precursors which are either active esters, amino acids, or amines, including a phenolic or imidazole substituent group in which one of the possible two sites on the group for radioiodination is substituted to permit production of a monoradioiodinated derivative. A preferred precursor is an active ester of 3-fluoro-5-radioiodotyrosine which can be coupled to a compound including an amino group to produce a monoradioiodinated derivative of the compound.

17 Claims, No Drawings

MONORADIOIODINATED DERIVATIVES AND PRECURSORS FOR PRODUCTION THEREON

This is a division of application Ser. No. 727,407, filed Sept. 29, 1976 now U.S. Pat. No. 4,120,867.

This invention relates to mono-radioiodinated precursors, intermediates employed for the preparation thereof and compounds having the precursors coupled thereto.

In a radioimmunoassay, the compound including a radioactive isotope of iodine is generally a compound which has the radioiodinated isotope substituted on a phenolic moiety. In the preparation of such radioiodinated compounds by conventional techniques, in general, the reaction mixture includes a monoiodo, diiodo and unreacted derivatives. In many cases, it is advantageous to employ monoiodo derivatives and, accordingly, there is a need for a means for conveniently producing such radioiodinated derivatives.

An object of the present invention is to provide monoradioiodinated compounds.

Another object of the present invention is to provide precursors suitable for coupling to a compound to provide a radioiodinated derivative of such compound.

A further object of the present invention is to provide radioiodinated derivatives of compounds suitable for use in radioassays.

These and other objects of the present invention should be more readily apparent from reading the following detailed description thereof.

In accordance with one aspect of the present invention, there is provided precursors which are either unlabeled or radiolabeled with a radioactive isotope of iodine, with the unlabeled precursors having a structure such that radioiodination thereof produces only a monoradioiodinated derivative, and with the labeled precursors being monoradioiodinated. The precursors are further characterized by structure such that they can be coupled to a compound including an amino or carboxygroup. The precursors of the present invention are represented by the following structural formula:

$$Y-R-COOX$$

$$Y-R-CH-COOX$$
$$\qquad\quad |$$
$$\qquad\quad NH-Z$$

$$Y-R-NH_2$$

$$Y-R-CH-COOA$$
$$\qquad\quad |$$
$$\qquad\quad NH_2$$

wherein R is a straight chain or branched chain divalent aliphatic hydrocarbon radical having from 1 to 6 carbon atoms;

X is hydrogen or an active ester moiety;
Z is either acyl or benzyloxy-carbonyl.
Y is either:

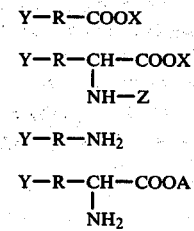

wherein one of $R_1$ and $R_2$ is either hydrogen or a radioactive isotope of iodine and the other of $R_1$ and $R_2$ is either lower (1–6 carbon atoms) alkyl, lower (1–6 carbon atoms) alkoxy, fluoro-, chloro-, bromo-, or nitro-;

A is either lower (1–6 carbon atoms) alkyl, an alkali metal (preferably sodium) or an alkaline earth metal and n is 0 or 1.

The radioactive isotope is preferably $^{125}I$, although other radioactive isotopes are also useful; e.g., $^{127}I$.

The compounds wherein one of $R_1$ and $R_2$ is a radioactive isotope of iodine are novel precursors.

The preferred precursors are the monoradioiodinated derivatives and in particular the active esters in that such precursors can be coupled to a compound, including an amino or carboxy group, to provide the corresponding monoradioiodinated derivative of such compound. Alternatively, and less preferred, the unlabeled precursor can be coupled to a compound, including an amino or carboxy group, followed by radioiodination of the resulting derivative to produce the corresponding monoradioiodinated derivative. The compounds having a precursor coupled thereto are represented by the following structural formulae:

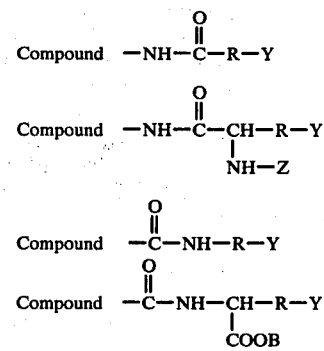

wherein B is lower alkyl and Y and R are as hereinabove described.

The compounds which are coupled with the precursors of the present invention, are preferably compounds for which an appropriate receptor can be found or the receptor, itself. The compounds can be:

(1) antigens, which when introduced into the blood stream of a vertebrate, result in the formation of antibodies;

(2) haptens, which when bound to an antigenic carrier and introduced into the blood stream of a vertebrate, produce antibodies specific for the hapten; or (3) compounds which have naturally occurring receptors and can be isolated in a form specific for the compound. It is to be understood that the compounds can have naturally occurring receptors and also function as a hapten when bonded to a protein.

Alternatively, as hereinabove noted, the antibody elicited in response to the antigen or hapten bound to a protein, or the naturally occurring receptor, can be coupled with the precursor material.

As representative compounds which can be coupled to the precursor in accordance with the present invention, there may be mentioned:

[1] drugs, including alkaloids; e.g., opiates, such as morphine heroin and the like; methadone and its analogs; indole alkaloids; catecholamines; barbiturates; glutethimide; cocaine and its metabolites and analogs;

diphenyl hydantoin; marijuana; tranquilizers, e.g. meprobamate; phenothiazines, etc.;

[2] amino acids, polypeptides, nucleotides, nucleosides and proteins, such as ACTH, oxytocin, luteinizing hormone, insulin, BenceJones protein, chorionic gonadotropin, pituitary gonadotropin, growth hormone, renin, thyroxine binding globulin, bradykinin, angiotensin, follicle stimulating hormone; thyroid stimulating hormone; cyclic AMP; etc.

[3] steroids, including: oestrogens, gestrogens, androgens, adrenocortical hormones, bile acids, cardiotonic glycosides, aglycones as well as saponins. As specific examples, these may be mentioned: testosterone, androsterone, equilenin, estrone, estriol, progesterone, pregnenolone, 17-hydroxy-deoxy-corticosterone (compound S), deoxycorticoserone, cortisone, corticosterone, cortisol, aldosterone, digoxigenin, digitoxigenin; etc.

[4] vitamins, such as Vitamin A, the B vitamin group, vitamin C, the D vitamins, and vitamins E and K; folic acid and miscellaneous biological substances, such as, antibodies, e.g., penicillin, tetracycline; antigens for Viral Hepatitis A and B. Rubella, Herpes Simplex, Alphafeto protein, antibodies to N gonorrhea, Dane Cores, etc.

The above substances are only representative, and it is understood that if the compounds do not include an amino or carboxy group for effecting coupling to the precursor the compound is employed as an appropriate analog which includes an amino or carboxy group for effecting coupling to the precursor.

The unlabeled precursors of the present invention are either known in the art or can be prepared by procedures known in the art. Thus, for example, the substituted hydroxyphenyl substituted acids, in particular 3-fluoro-4-hydroxyphenylpropionic acid can be prepared by converting 3-fluoro-4-methoxybenzaldehyde to 3-fluoro-4-methoxycinnamic acid, which can be reduced to 3-fluoro-4-methoxyphenylpropionic acid, followed by hydrolysis.

The active ester precursors are prepared by procedures known in the art. The active ester may be any one of a wide variety of active esters which are suitable for coupling the precursor to an amino group. The active esters are well-known in the art; for example, such esters are described in "Recent Trends in the Synthesis of Linear Peptides" by A. Kapoor J. Pharm. Science 1970 59 (1) pages 1-27, and the selection of an appropriate active ester is deemed to be within the scope of those skilled in the art from the teachings herein. The preferred active esters are prepared from chloro- or nitro substituted phenols or N-hydroxysuccinimide; however, the invention is not limited to such preferred groups.

The precursors are coupled to the compounds by procedures known in the art. For example, the active ester precursors are coupled by reaction of the active ester precursor with the compound in a suitable buffer (pH 6-9) at temperatures of from $-10°$ to $15°$ C. The precursors which do not contain active ester groups can be coupled by the use of a suitable coupling agent; e.g., dicyclohexylcarbodimide, or by the mixed anhydride technique. A glycoside, such as digoxin, may be coupled to the precursor by opening the sugar portion of the glycoside by the use of periodate, followed by coupling of the resulting dialdehyde to an amino precursor, with such a technique generally being described by Haber, *Biochemistry* Vol. 9, No. 2, Jan. 20, 1970.

The technique for coupling the precursors to produce the coupled compounds of the present invention are well known in the art and no further details in this respect are required for a complete understanding of the present invention.

The compounds including the coupled monoradioiodinated substituent are suitable for use in a radioassay by procedures known in the art. Thus, the coupled radioiodinated compounds of the present invention may be employed for a radioassay in a manner identical to the radioiodinated compounds employed in prior art radioassays.

The assay employing the monoradioiodinated coupled compound is effected by general procedures known in the art, which involve:

[1] combining receptor, sample, and monoradioiodinated labeled substance;

[2] determining the radioactive properties of the bound or free portion; and

[3] comparison of such properties with a standard.

Prior to determining the radioactive properties of the bound or free portion, it is preferred to effect separation of such bound and free portions by procedures known in the art. Thus, for example, such separation may be effected by the use of solid adsorbents, gel filtration, ion exchange resins, etc. Alternatively, the receptor may be bound to a suitable substrate to facilitate separation.

The receptors employed in the assay, as known in the art, are, in the most part, macromolecules which recognize specific structures, with such receptors generally being proteins and nucleic acids which are found in cell membranes, blood and other biological fluids.

The most generally used group of receptors are antibodies, which are conveniently used in the assay of haptens and antigens. The antibodies are produced by introducing an immunogenic substance into the bloodstream of a living animal and there are many materials which act as antigens to produce an immunogenic response. Haptens can also be employed to prepare antibodies by procedures well known in the art. In general, such a procedure involves bonding the hapten to a protein, followed by introduction thereof into the bloodstream to produce antibodies for the hapten; i.e., the compound bonded to the protein. The antibody thus generated, as known in the art, can be employed as a receptor in an assay for the hapten.

In addition to antibodies, there are many naturally occurring materials which are specific to compounds of biological interest and can be used in the assay of the present invention. Thus, for example, as known in the art, there are naturally occurring receptors which are suitable for the assay of materials, such as, folates, thyroxine, corticosterone, cortisone, estrogen, insulin, angiotensin.

The use of receptors in an assay for various compounds is well known in the art and no further details in this respect are deemed necessary for an understanding of the present invention.

The invention will be further described with respect to the following examples; however, the scope of the invention is not to be limited thereby:

EXAMPLE 1

I—Preparation of 3-fluoro-4-methoxy-cinnamic acid

A mixture of 3-fluoro-anisaldehyde (1.5 g) and malonic acid (2.08 g) in 5 ml pyridine was warmed until clear solution was obtained. To this mixture piperidine (0.4 ml) was added and then the content of the flask was heated at 80° C. for one (1) hour. It was further refluxed for 3 hours. At the end of this period the mixture was poured into 50 ml of cold water. It was then acidified by adding 5 ml of concentrated hydrochloric acid. Upon addition of acid, the solid separated, which was filtered and washed with cold water. The material was dried. Yield 1.7 g. The crude material was crystallized from a mixture of tetrahydrofuran and water. m.p. 227°–230° C.

II—Preparation of 3-(3-fluoro-4-methoxyphenyl)propionic acid 2.0 g of 3-fluoro-4-methoxy cinnamic acid was dissolved in 100 ml ethyl alcohol. To this was added 100 mg of platinum oxide as a catalyst. The mixture was hydrogenated in a Parr apparatus for 90 minutes. After the hydrogenation was over, the mixture was filtered and concentrated. The solid was crystallized by adding water. Yield=1.63 g, m.p. 107°–112° C.

III—Preparation of 3-(3-fluoro-4-methoxyphenyl)propionic acid.

To 1.0 gm of 3-fluoro-4-methoxyphenyl propionic acid (II) in a 50 ml round bottom flask, 15.0 ml of HI (47–51%) was added and the mixture was heated at 140° C. for 1 hour. At the end of 1 hour, the mixture was concentrated and 25 to 30 ml water was added. It was again concentrated using a rotary evaporator. Finally 50 ml water was added and the pH was adjusted to 3 by adding sodium bicarbonate. The aqueous mixture was then extracted with benzene and the benzene layer was washed twice with water. Finally, the benzene layer was dried over anhydrous sodium sulfate. The benzene was evaporated off. The product was in the oily form and was used in the next step for the preparation of active ester.

IV—Preparation of N-succinimidyl-3-(3-fluoro-4-hydroxyphenyl)propionate.

3-(3-fluoro-4-hydroxyphenyl)propionic acid (1.08 g) and N-hydroxysuccinimide (1.15 g) in tetrahydrofuran (7.0 ml) was treated at −18° C. with dicyclohexylcarbodiimide (2.47 g). The mixture was stirred at −18° C. for 2 hours, kept at room temperature for 10 hours and treated with acetic acid (0.12 ml) to destroy excess of carbodiimide. After 1 hour, the mixture was diluted with ethyl acetate (10 ml). The dicyclohexyl urea was filtered. The ethyl acetate layer was evaporated to dryness. The residual oil was then crystallized from ethyl acetate/petroleum ether. m.p. 100°–102° C.

V—Radioiodination of active ester.

The reaction is carried out at room temperature (about 20° C.) N-succinimidyl-3-(3-fluoro-4-hydroxylphenyl)propionic acid (0.2 to 0.025 mg) was treated with 2 to 5 mCi of $NaI^{125}$ and 50 μg of chloramine-T in 10 μl of 0.25 M phosphate buffer pH 7.5. The reaction was immediately terminated by the addition of 120 μg of sodium metabisulfite in 10 μl of 0.05 M phosphate buffer, pH 7.5, after which 200 mg of carrier KI in 100 μl of the above buffer was added. The reaction mixture was extracted into two portions of 0.25 ml of dry benzene containing 10 μl of dimethyl-formamide. This solution was then transferred into a V-shaped glass vial containing a magnetic flea for further use.

VI—Coupling of $I^{125}$-active ester to thyroid stimulating hormone (TSH).

2.5 mCi of $I^{125}$ active ester (step 5) was transferred into a V-shaped vial containing a magnetic flea and the vial was sealed using a Teflon-septum cap. The benzene was then evaporated by passing a slow stream of $N_2$ gas while trapping any volatile radio activity in an attached charcoal trap. The cap from the vial was removed and added 10 μl (5 μg) of hTSH (human TSH) solution and 2 μl of 0.5 M sodium borate buffer pH 8.5. The mixture was stirred at 4° C. for 20 minutes. 10 μl of 0.1 M sodium borate buffer-pH 8.5 was added to the reaction vial and stirred at 4° C. for 5 minutes. 0.5 ml of 0.2 M glycine solution was added to the reaction mixture and stirred at 4° C. for an additional 5 minutes. At this point, the reaction is over. This mixture was transferred to a Sephadex-G-75 column (size 90×1.7 cm) and the column was eluted at 4° C. with 0.05 M sodium phosphate buffer (pH 7.5) containing 0.25% gelatin. The appropriate peak for hTSH was separated and stored separately for further use in radioimmunoassay.

EXAMPLE 2

Testosterone 3-(0-carboxymethyl)oxime-3-fluoro-tyrosinemethyl ester $I^{125}$ (a) Preparation of 3-fluoro-tyrosine-$I^{125}$ Three milligrams of 3-fluoro-tyrosine HCl was dissolved in 5 ml phosphate buffer (0.5 M, pH 7.5). Ten microliter of this solution in a suitable vial was treated with 5 mCi of $NaI^{125}$ followed by 10 μl of chloramine-T solution of 50 mg/10 ml concentration. After 60 seconds, 10 μl of sodium metabisulfite solution of concentration 300 mg/10 ml was added to terminate the reaction.

(b) Steroid activation

To 2.5 mg of testosterone-3-(0-carboxymethyl)oxime in a tube, 50 μl of dioxane, 10 μl of prediluted tributylamine (1 ml t-butylamine/9 ml dioxane) and 10 μl of prediluted isobutyl chloroformate (1 ml of isobutyl chloroformate/3 ml dioxane) were added. The reaction mixture was stirred at 10° C. for 20 minutes.

(c) The solution in (b) was diluted to 3.43 ml using dioxane and 50 μl of this diluted solution was added to the solution in (a) followed by 10 μl of 0.1 N NaOH solution. The entire reaction mixture was maintained at 0° C. for 2 hours. The reaction mixture was then acidified with 0.1 N HCl (0.9 ml) and extracted with 1 ml toluene. The organic layer was discarded. To the aqueous layer, 0.9 ml of 0.1 N NaOH and 1 ml of 0.5 M phosphate buffer (pH 7.0) were added. The aqueous layer was extracted with ethyl acetate. The ethyl acetate layer contained the final product.

EXAMPLE 3

Testosterone-17-β-0-succinyl-3-fluoro-tyrosine methyl ester.

(a) A mixture of 7.5 mg of testosterone-17-β-hemisuccinate, 6 mg 3-fluoro-tyrosine methyl ester. HCl and 6 mg of EDC (1-ethyl-3-(dimethylaminopropyl carbodiimide. HCl) in a vial containing 0.3 ml tetrahydrofuran and 0.05 ml water, was stirred at the room temperature for 90 minutes. Then it was purified by preparative chromatography using silica gel plates. Solvent system, $CHCl_3$:MeOH:$H_2O$=180:20:0:2. The product, $R_f$ value of 0.52, was isolated by extracting the silica gel zone with ethanol.

By using a similar procedure, several other derivatives were made, e.g., testosterone-17-β-0-succinyl-3-fluoro-tyrosine ethyl ester and testosterone-17-β-3-fluoro-tyrosine-t-butyl ester.

(b) Preparation of testosterone-17-β-0-succinyl-3-tyrosine methyl ester $I^{125}$ The product (a) described above was iodinated as follows:

The alcoholic solution of product (a) 10, mole in 10 μl was taken into a small vial containing 50 μl phosphate buffer (0.5 M pH 7.5). To this 25 μl of chloramine-T solution was added (10 mg/3 ml) followed by 5 μl of $NaI^{125}$. After 30 seconds the reaction was terminated by adding 25 μl of sodium metabisulfite solution (30 mg/3 ml). The product was purified by thin layer chromatography using silica gel coated plates and running it in $CHCl_3:MeOH:H_2O = 180:20:0:2$ as a solvent system.

EXAMPLE 4

Aldosterone-3(0-carboxymethyl)oxime-3-fluoro-tyrosine methyl ester-$I^{125}$ (a) Steroid activation To 1.5 mg of aldosterone-3(0-carboxymethyl)oxime in a tube, 50 μl of dioxane was added as a solvent. To the above reaction mixture 10 μl of prediluted tributyl-amine (1 ml tributylamine/15 ml dioxane) and 7 μl of prediluted isobutyl chloroformate (1 ml of isobutyl chloroformate in 6 ml dioxane) was added and the reaction mixture was stirred at 10° C. for 20 minutes.

(b) Coupling

The solution (a) from above reaction was diluted by adding 1 ml of dioxane. 50 μl of this diluted solution was added to solution (a) of Example 2 followed by the addition of 10 μl solution of 0.1 N NaOH. The entire reaction mixture was maintained at 0° C. for 2 hours. The reaction mixture was then acidified with 0.1 N HCl (0.9 ml) and extracted with 1 ml toluene. The organic layer was discarded. To the aqueous layer was added 0.9 ml of 0.1 N NaOH and 1 ml of 0.5 molar phosphate buffer (pH 7.0). The aqueous layer was extracted with ethyl acetate. The ethyl acetate layer contained the final product.

EXAMPLE 5

Digoxin-3-fluoro-tyrosine methyl ester—$I^{125}$.

600 mg of digoxin was suspended in 30 ml of absolute ethanol. To this suspension was added slowly 30 ml of 2% sodium periodate in water. The reaction mixture was stirred for 1 hour. After 1 hour, it was evaporated to dryness. The residue was dissolved in 5.0 ml water and then extracted with ethyl acetate. The ethyl acetate layer was dried over sodium sulphate and evaporated to dryness to yield the solid dialdehyde. 250 mg of the dialdehyde was dissolved in 10 ml methanol. To this, 3-fluoro-tyrosine methyl ester (65 mg) and 50 mg of sodium cyanoborohydride was added. The pH of the reaction mixture was about 7.3. The reaction mixture was stirred for 90 minutes at room temperature. The pH was lowered from 8.2 to 7.2 by adding 0.05 N HCl solution. The reaction mixture was concentrated to dryness, 10 ml of water was added and the aqueous layer was then extracted with ethyl acetate. The ethyl acetate layer was dried and concentrated. The product was crystallized from ethyl acetate/ether.

Radioiodination.

To 2.0 mg of the above product in 20 ml of methanol in a vial, 5 mCi $NaI^{125}$ was added followed by 100 μg of chloramine-T. The reaction was terminated by adding 300 μg of sodium metabisulfite solution. The product was purified by thin layer chromatography using silica gel plates. Solvent system, ethyl acetate:methanol=96.4.

EXAMPLE 6

(a) Preparation of cholylglycyl-3-fluoro-tyrosine methyl ester.

A mixture of 46 mg of cholylglycine, 25 mg of 3-fluoro-tyrosine methyl ester and 65 mg of EDC (1-ethyl-3-(dimethylamino propyl) carbodiimide HCl was stirred magnetically in 300 μl tetrahydrofuran and 75 μl of water. The stirring was stopped after 2 minutes. The mixture was extracted with 3 ml ethyl acetate. The ethyl acetate layer was washed with water, dried over sodium sulfate and then concentrated to dryness; yield—40 mg R$_f$; 0.44 solvent system $CHCl_3:MeOH$ 8:2

(b) Preparation of cholylglycyl-3-fluoro-tyrosine (saponification of product 6(a).

A mixture of cholylglycyl-3-fluoro-tyrosine methyl ester (Example 6(a)), 200 μl dioxane and 200 μl of 2.5 N NaOH was stirred for 30 minutes at room temperature. The pH was adjusted to 2 to 3 with 6 N HCl. The aqueous layer was extracted with ethyl acetate. The ethyl acetate layer was washed with water, dried over sodium sulfate and evaporated to dryness.

(c) Preparation of $I^{125}$ Cholylgycyl-3-fluoro-tyrosine.

Seven mg of cholylglycyl-3-fluoro-tyrosine was dissolved in 3.5 ml ethyl alcohol and a 5 μl aliquot was mixed in a small vial with 50 μl of 0.5 M phosphate buffer (pH 7.4) and 1.8 mCi of $NaI^{125}$. Ten (10) μl of chloramine-T solution (15 mg/5 ml water) was added and, after 60 seconds, the reaction was terminated by adding 10 μl of sodium metabisulfite (25 mg/5 ml water). The reaction mixture was applied to a Dowex 1×8 resin column. After washing with water, the product was eluted with methanol containing 1% acetic acid.

EXAMPLE 7

Labeling of antibody (a) Preparation of N-succinimidyl-3(3-fluoro-4-hydroxyphenyl)propionate-$I^{125}$ N-succinimidyl-3(-3-fluoro-4-hydroxyphenyl)propionate (1.32 mg) was dissolved in 10 ml ethyl acetate. Twenty (20) μl of this solution was transferred to a small vial and N$_2$ gas was slowly bubbled until all the ethyl acetate had evaporated. To this residue, 20 μl of 0.5 M phosphate buffer (pH 7.4) was added followed by 10 mCi of $NaI^{125}$ and 5 μl of chloramine-T solution (25 mg/5 ml water). After 5 seconds, the reaction was terminated by adding 10 μl of KI solution (100 mg/5 ml) and 5 μl of dimethyl formamide. This mixture was extracted twice with 0.6 ml dry benzene. The benzene layer was separated, dried with anhydrous sodium sulfate, and charged to a small column containing $CaCO_3$. The column was eluted with benzene. The first 5.0 ml collected contained the pure product.

(b) Coupling of active ester to antibody 0.25 mCi in 63 μl of benzene of the active ester-I$^{125}$ in Example 7(a) was evaporated with N$_2$ gas. The vial was cooled in icewater and 1 ml of rabbit IgG solution (1 mg of IgG/1 ml 0.1 M borate buffer pH 8.5) was added to the vial. The solution was stirred at 4° C. for 25 minutes and then treated with 0.5 ml of 0.2 M glycine solution. The reaction mixture was stirred for 10 minutes at 4° C. and the content of the tube was charged to a Sephadex G-25 column at 4° C. The column was eluted with 0.1 M phosphate buffer (pH 7.4) containing 0.1% BSA and 0.02% sodium azide. The rate of column elution was adjusted to 10 ml per hour and 1 ml volume fractions were collected. The product was eluted at fraction numbers 68 to 74.

The present invention is particularly advantageous in that it is possible to easily produce monoradioiodinated derivatives of compounds which can be used as the tagged or labeled compound in a radioassay.

A monoradioiodinated derivative is advantageous, as compared to diradioiodinated derivatives, in that the monoradioiodinated derivatives have improved stability and longer half-lives. In addition, the monoradioiodinated derivatives are altered less and for a given specific activity insures good physiological parameters. In addition, the precursors can be prepared with an excess of the radioactive isotope to minimize production of unlabeled precursor, without production of diiodo derivative.

In addition, the radioiodination can be effected with two different radioisotopes; e.g., $^{125}$I and $^{127}$I, and by adjusting the ratio thereof, it is possible to obtain a desired specific activity.

These and other advantages should be more apparent from the herein description of the present invention.

Numerous modifications and variations of the present invention are possible in light of the above teachings and, therefore, within the scope of the appended claims, the invention may be practiced otherwise than as particularly described.

What is claimed is:

1. A tracer for a radioassay comprising a compound having a radioiodinated substituent group selected from the group consisting of:

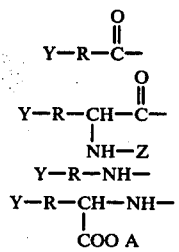

wherein:
R is selected from the group consisting of straight and branched chain aliphatic hydrocarbons having from 1 to 6 carbon atoms;
X is selected from the group consisting of hydrogen and active ester moieties;
Z is selected from the group consisting of acyl or benzyloxycarbonyl;
Y is selected from the group consisting of:

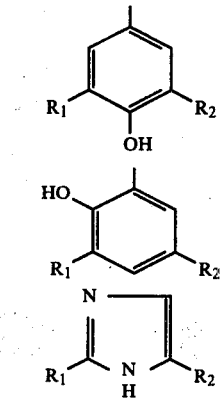

wherein one of R$_1$ and R$_2$ is a radioisotope of iodine and the other of R$_1$ and R$_2$ is selected from the group consisting of lower alkyl, lower alkoxy, fluoro-, chloro-, bromo-, and nitro-;
A is selected from the group consisting of hydrogen, lower alkyl, an alkali metal and an alkaline earth metal;
said substituent groups (a) and (b) being linked to the compound through an amino group and said substituents (c) and (d) being linked to the compound through a

group, said compound being selected from the group consisting of antigens, haptens, antibodies and compounds having naturally occurring receptors.

2. The tracer of claim 1 wherein the substituent group has structural formula (a).

3. The tracer of claim 1 wherein the substituent group has structural formula (b).

4. The tracer of claim 1 wherein the substituent group has structural formula (c).

5. The tracer of claim 1 wherein the substituent group has structural formula (d).

6. The tracer of claim 1 wherein one of R$_1$ and R$_2$ is lower alkyl and the other of R$_1$ and R$_2$ is a radioisotope of iodine.

7. The tracer of claim 1 wherein one of R$_1$ and R$_2$ is fluorine and the other of R$_1$ and R$_2$ is a radioactive isotope of iodine.

8. The tracer of claim 1 wherein the radioactive isotope of iodine is $^{125}$I.

9. The tracer of claim 1 wherein R is a straight chain aliphatic hydrocarbon having 3 carbon atoms.

10. The tracer of claim 1 wherein Y has structural formula I.

11. The tracer of claim 1 wherein Y has structural formula II.

12. The tracer of claim 1 wherein Y has structural formula III.

13. The tracer of claim 1 wherein the compound is an antigen.

14. The tracer of claim 1 wherein the compound is a hapten.

15. The tracer of claim 1 wherein the compound is an antibody.

16. The tracer of claim 1 wherein the compound is a compound having a naturally occurring receptor.

17. In a radioassay employing a radioiodinated tracer, the improvement comprising:
employing as said tracer a tracer as defined in claim 1.

* * * * *